United States Patent
Pyun et al.

(10) Patent No.: US 10,857,377 B2
(45) Date of Patent: Dec. 8, 2020

(54) LASER DEVICE AND LASER OUTPUT CONTROL METHOD THEREIN

(71) Applicant: Speclipse, Inc., Seoul (KR)

(72) Inventors: Sung Hyun Pyun, Seoul (KR); Wanki Min, Gyeonggi-do (KR); Hyoung Soo Shin, Seoul (KR)

(73) Assignee: Speclipse, Inc., Seoul (KR)

( * ) Notice: Subject to any disclaimer, the term of this patent is extended or adjusted under 35 U.S.C. 154(b) by 358 days.

(21) Appl. No.: 15/948,545

(22) Filed: Apr. 9, 2018

(65) Prior Publication Data

US 2019/0015681 A1     Jan. 17, 2019

(30) Foreign Application Priority Data

Jul. 12, 2017 (KR) .................. 10-2017-0088575

(51) Int. Cl.
*A61N 5/06* (2006.01)
*A61B 18/20* (2006.01)
(Continued)

(52) U.S. Cl.
CPC .......... *A61N 5/0616* (2013.01); *A61B 18/203* (2013.01); *A61B 2017/00057* (2013.01);
(Continued)

(58) Field of Classification Search
CPC .......... A61N 5/0616; A61N 2005/0626; A61N 2005/0644; A61N 2005/0666;
(Continued)

(56) References Cited

U.S. PATENT DOCUMENTS

2012/0283709 A1* 11/2012 Reichert .............. A61N 5/0616
606/9
2014/0072015 A1    3/2014 Han et al.

FOREIGN PATENT DOCUMENTS

JP      H07-221373 A    8/1995
JP      2008-296256 A   12/2008
(Continued)

OTHER PUBLICATIONS

Office Action dated Aug. 16, 2017, issued in Korean Patent Application No. 10-2017-0088575, with English Translation.
(Continued)

*Primary Examiner* — Lindsey G Wehrheim
(74) *Attorney, Agent, or Firm* — Harness, Dickey & Pierce, P.L.C.

(57) ABSTRACT

The present disclosure relates to a method and a device for controlling a laser output. According to an embodiment, there are provided a method for controlling a laser output of a laser device, provided with a laser generator and a handpiece for radiating a laser generated at the laser generator onto a target, and a device performing the method. The method includes the steps of: measuring, by a plurality of distance sensors arranged along a circumference of one end of the handpiece from which the laser is outputted, distances between the plurality of distance sensors and the target; based on the distances between the distance sensors and the target, calculating an effective area which is a region of the target onto which the laser is really radiated; and increasing or reducing the laser output to radiate the laser onto the effective area with a predetermined energy density.

12 Claims, 6 Drawing Sheets

(51) Int. Cl.
    *A61N 5/067*     (2006.01)
    *A61B 18/00*     (2006.01)
    *A61B 17/00*     (2006.01)

(52) U.S. Cl.
    CPC .............. *A61B 2017/00106* (2013.01); *A61B 2018/00452* (2013.01); *A61B 2018/00642* (2013.01); *A61B 2018/00785* (2013.01); *A61N 2005/063* (2013.01); *A61N 2005/067* (2013.01); *A61N 2005/0626* (2013.01); *A61N 2005/0644* (2013.01); *A61N 2005/0666* (2013.01); *A61N 2005/0667* (2013.01)

(58) Field of Classification Search
    CPC ...... A61N 2005/0667; A61N 2005/067; A61N 2005/063; A61B 18/203; A61B 2017/00057; A61B 2017/00106; A61B 2018/00452; A61B 2018/00643; A61B 2018/00785
    See application file for complete search history.

(56) References Cited

FOREIGN PATENT DOCUMENTS

| | | |
|---|---|---|
| JP | 5154145 B2 | 2/2013 |
| KR | 10-2005-0102524 A | 10/2005 |
| KR | 10-2010-0132841 A | 12/2010 |
| KR | 10-2012-0012194 A | 2/2012 |
| KR | 10-1227153 B1 | 1/2013 |
| KR | 10-2016-0126949 A | 11/2016 |

OTHER PUBLICATIONS

Office Action from corresponding Korean Patent Application No. 10-2017-0088575, dated Aug. 16, 2017.
Office Action from corresponding Korean Patent Application No. 10-2017-0077847, dated Aug. 16, 2017.
Notice of Allowance from corresponding Korean Patent Application No. 10-2017-0077847, dated Nov. 27, 2017.
Notice of Allowance from corresponding Korean Patent Application No. 10-2017-0088575, dated Dec. 27, 2017.
International Search Report from corresponding PCT Application No. PCT/KR2018/002995, dated Jun. 22, 2018.

\* cited by examiner

LASER DEVICE AND LASER OUTPUT CONTROL METHOD THEREIN

CROSS REFERENCE TO RELATED APPLICATION

The present application claims priority to Korean Patent Application Nos. 2017-0088575, filed Jul. 12, 2017 in the Republic of Korea, the disclosures of which are incorporated herein by reference.

FIELD

The present disclosure relates to a laser device, and more particularly, to a laser device with a laser output controller and a laser output control method therein.

The present disclosure was supported by National Research and Development Project Business of Ministry of Trade, Industry and Energy as follows:

[Project Number] N056300067
[Related Department] Ministry of Trade, Industry and Energy
[Research Management Specialized Agency] Korea Institute for Advancement of Technology
[Research Business Name] 2017 Commercialization Connection Technology Development Business (R&BD) Private Investment Connection Form (Take-off Platform-TOP)
[Research Project Title] Development and Commercialization of Real-Time and Non-invasive Skin Cancer Diagnosis Device Based On Laser-Induced Plasma/Fluorescence Spectroscopy
[Contribution Rate] 1/1
[Main Institute] Speclipse, Inc.
[Research Period] Apr. 1, 2017-Dec. 31, 2018

BACKGROUND

Laser devices for treatment and operation in the medical field or for beauty treatment in the field of beauty care are widely used in recent years. The laser device for laser treatment and procedure for operation or beauty treatment generates a laser beam having a predetermined wavelength and an energy density (energy per unit area), and radiates the laser beam onto a target (for example, a skin to be treated/for procedure) through a handpiece.

However, there is a difference in characteristics between a laser beam outputted from the laser device and a laser beam radiated onto a real target. In a normal laser handpiece 10 of FIG. 1, for example, a tip 20 including a base 21, a support 22, and a guide portion 23 is attached to a leading end of the handpiece 10. A user holds the handpiece 10 in an upright position with respect to a target (for example, a skin S) as shown in FIG. 1, and controls the handpiece 10 to radiate a laser with the guide portion 23 being in contact with the skin S. That is, a height from a lowermost portion of the handpiece 10 (that is, a lower end of the base 21 of the tip 20) to the skin S is constantly maintained as a distance H by the support 22 and the guide portion 23. A laser output is set with reference to this state.

However, it may be difficult for the user to always maintain the handpiece 10 in the upright position with respect to the target during a treatment as shown in FIG. 1, and there is a real problem that the distance to the skin S is not always maintained constantly.

Referring to FIG. 2A, a laser device may be designed to radiate a collimated beam L1 having the same energy density (J/cm2) over the cross-sectional area of the laser. However, in this state, a laser really outputted from the handpiece 10 may be radiated in such a pattern that its cross-sectional area increases or is reduced according to a distance like the form of a laser L2 of FIG. 2A. In this case, a region A of the target onto which the laser L2 is radiated varies according to the distance H, and thus the energy density of the laser received by the real skin differs from an initially set energy density.

In addition, even if a laser device is designed to radiate a laser L3 in the form of a defocused beam (or in the form of a focused beam) as shown in FIG. 2B, a laser radiation region A varies according to the distance H to the skin S, and accordingly, the energy density of the laser received by the skin S is greatly changed according to the distance to the handpiece, and thus a constant and stable treatment effect may not be obtained.

Therefore, when the laser device is used for medical purpose or beauty care purpose, it is important to always maintain a real energy density of a laser as a predetermined energy density on a treatment region in order to more exactly and safely use the device and to achieve a predetermined treatment effect even if the handpiece is titled or the distance to the skin is changed.

SUMMARY

Technical Objects

According to an embodiment of the present disclosure, there is provided a laser device which has a plurality of distance sensors mounted on a leading end of a handpiece, and calculates a slope and a distance of the handpiece based on distance values measured by the distance sensors, and calculates an effective area of a target, and thereby controls a laser output to always maintain an energy density constantly.

Technical Solving Means

According to an embodiment of the present invention, there is provided a method for controlling a laser output of a laser device provided with a laser generator and a handpiece for radiating a laser generated at the laser generator onto a target, the method including the steps of: measuring, by a plurality of distance sensors arranged along a circumference of one end of the handpiece from which the laser is outputted, distances between the plurality of distance sensors and the target; based on the distances between the distance sensors and the target, calculating an effective area which is a region of the target onto which the laser is really radiated; and increasing or reducing the laser output to radiate the laser onto the effective area with a predetermined energy density.

According to an embodiment of the present invention, there is provided a laser device including: a laser generator configured to generate a laser; a controller configured to control an output of the laser generated at the laser generator; a handpiece configured to output the laser generated at the laser generator through one end thereof; and a plurality of distance sensors attached along a circumference of the one end of the handpiece, wherein the controller is configured to calculate an effective area which is a region of a target onto which the laser is really radiated, based on distances to the target measured by the plurality of distance sensors, and to increase or reduce a laser output to radiate the laser onto the effective area with a predetermined energy density.

Advantageous Effect

According to an embodiment of the present disclosure, the effective area of the target may be calculated based on distance measurement values measured by the distance sensors mounted on the handpiece, and a laser output value may be obtained to obtain a predetermined energy density based on the effective area. Therefore, even when the handpiece is tilted or a distance to the target is changed, a target energy density can be always maintained constantly.

According to an embodiment of the present disclosure, when one or more measurement values measured by the distance sensors are greater than a predetermined distance value or the slope of the handpiece is less than a predetermined angle, the laser output may be temporarily stopped, such that an accident caused by a laser can be prevented in advance, and a predetermined medical/beauty care effect can be achieved.

DETAILED DESCRIPTION

Figure 1:
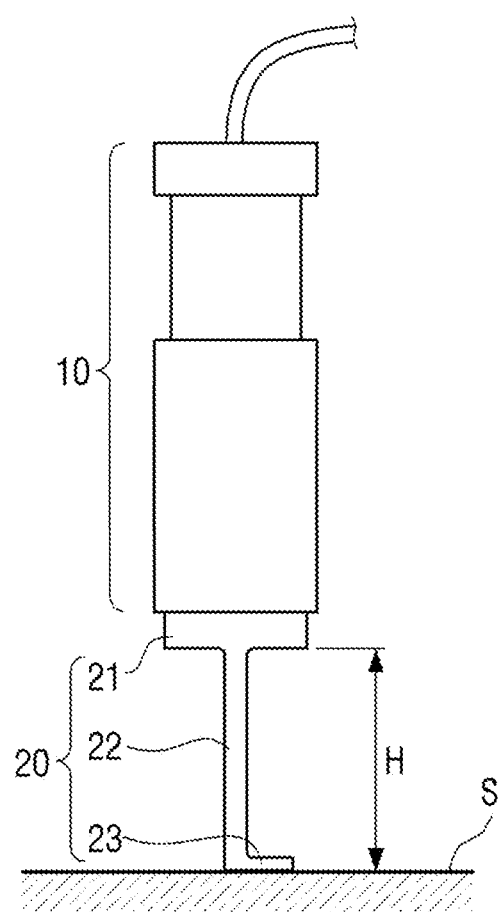
FIG. 1 is a view to explain a handpiece of a related-art laser device.
Figure 2A:
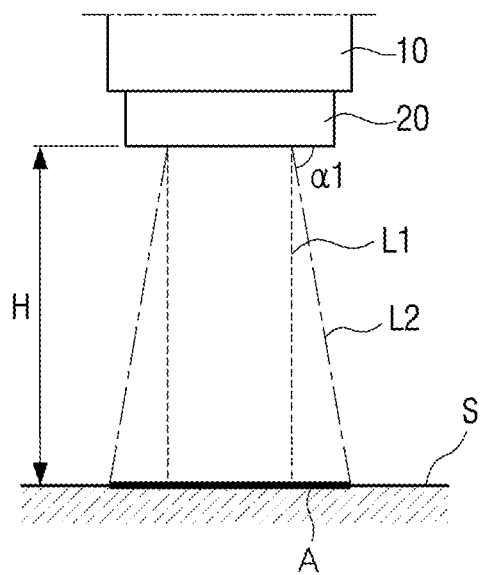
FIGS. 2A and 2B are views showing an example of a laser form outputted from a handpiece.
Figure 2B:
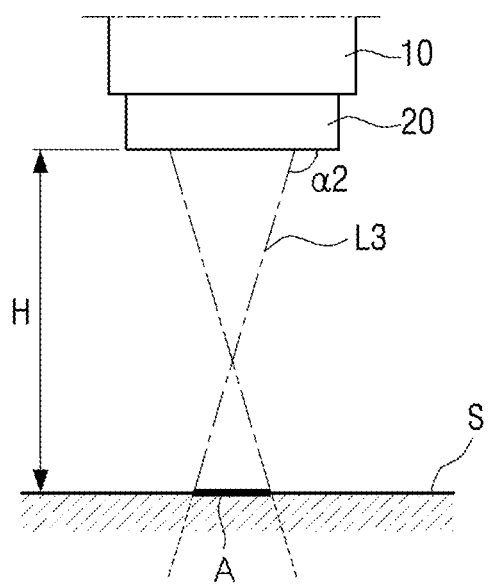

Exemplary embodiments will now be described more fully with reference to the accompanying drawings to clarify aspects, other aspects, features and advantages of the present disclosure. The exemplary embodiments may, however, be embodied in many different forms and should not be construed as limited to the exemplary embodiments set forth herein. Rather, the exemplary embodiments are provided so that this disclosure will be thorough and complete, and will fully convey the scope of the application to those of ordinary skill in the art.

In the drawings of the present disclosure, lengths, thicknesses, and wideness of elements may be exaggerated for easy understanding of technical features.

As used herein, the singular forms are intended to include the plural forms as well, unless the context clearly indicates otherwise. It will be further understood that the terms "comprise" and/or "comprising," when used in this specification, do not preclude the presence or addition of one or more other components.

It will be understood that when an element is referred to as being "on" another element, the element can be directly on another element or intervening elements. The terms "unit" and "module" and the terms having suffix "-er" or "-or" used in the description of this application refer to a unit for processing at least one function or operation, and may be implemented by hardware, software, or a combination of hardware and software.

Hereinafter, the present disclosure will be described in greater detail with reference to the accompanying drawings. In describing specific embodiments, various specific features are described to assist in a detailed description and a comprehensive understanding of the present disclosure. However, it is apparent that the exemplary embodiments can be carried out by those of ordinary skill in the art without those specifically defined features. In the description of exemplary embodiments, certain detailed explanations of portions which are well known and have nothing to do with the present disclosure are omitted when it is deemed that they may unnecessarily obscure the essence of the present disclosure.

Figure 3:
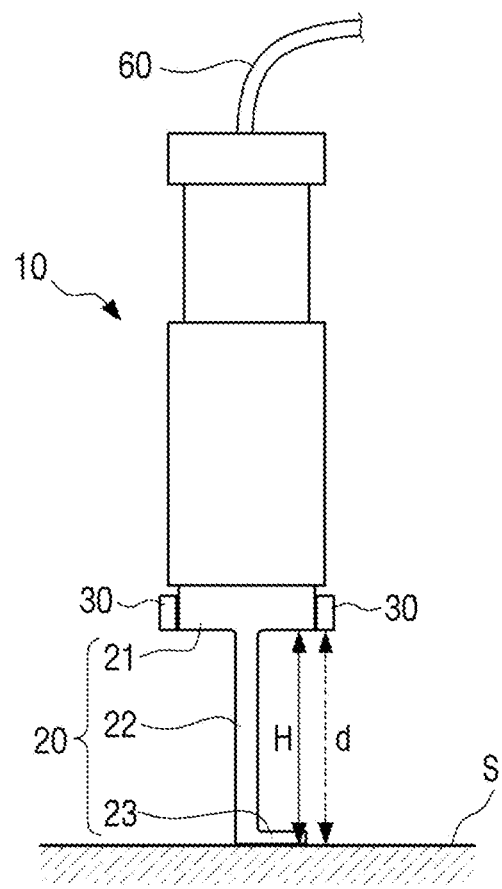
FIGS. 3 and 4 are views to explain a handpiece according to an embodiment of the present disclosure.
Figure 4:
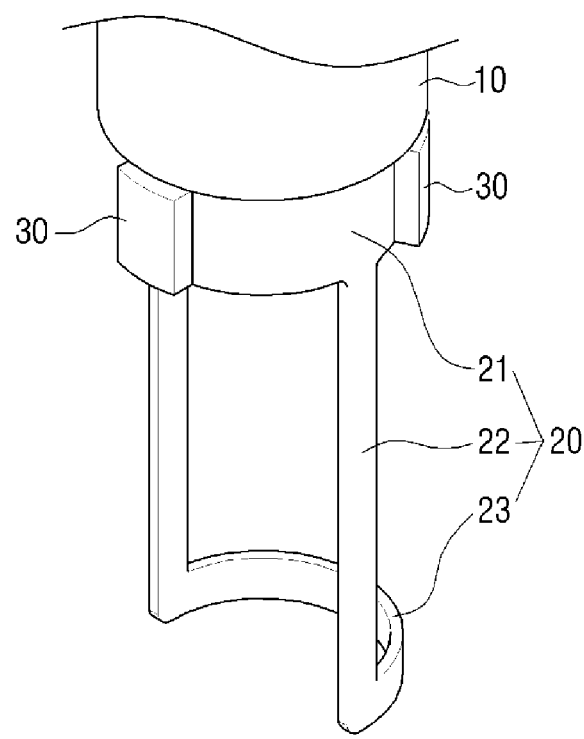
Figure 5:
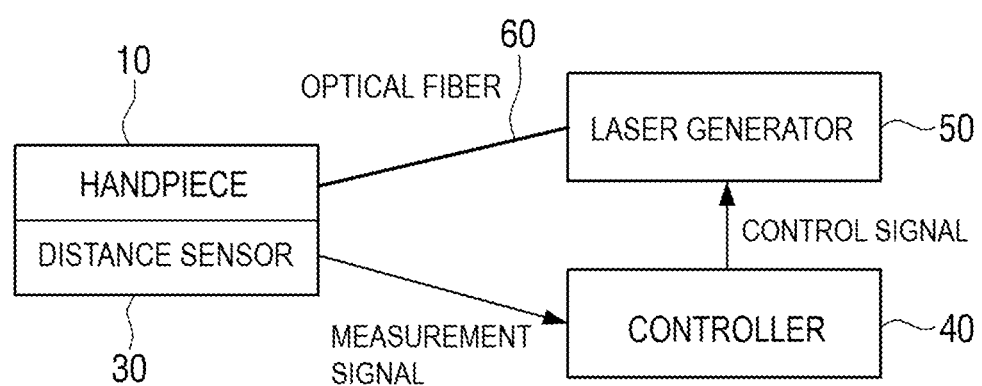
FIG. 5 is a block diagram of a laser device according to an embodiment of the present disclosure.

FIGS. 3 and 4 are views schematically showing a handpiece according to an embodiment of the present disclosure, and FIG. 5 is a block diagram of an example of a laser device including the handpiece.

Referring to the drawings, the handpiece 10 according to an embodiment is a member that has a substantially cylindrical shape so as to allow a user to hold with user's hand, and an optical fiber 60 may be connected to one end (an upper end in FIG. 3) of the handpiece 10, and a laser generated at a laser generator 50 (see FIG. 5) may be guided to the handpiece 10 through the optical fiber 60, and then may be outputted through the other end (a lower end in FIG. 3) of the handpiece 10.

The handpiece 10 may have a plurality of optical elements arranged therein to guide a laser, such as an optical fiber, a lens, a mirror, etc. Light outputted from the handpiece 10 may be any one of a collimated beam, a focused beam, or a defocused beam, and an energy density, a wavelength, etc. of the laser may vary according to a specific implementation situation where a laser device is used.

In the illustrated embodiment, a tip 20 may be attached to the lower end of the handpiece 10. The tip 20 may be attachably or detachably coupled to the handpiece 10. In an embodiment, the tip 20 may include a base 21 coupled to the lower end of the handpiece 10, a support 20 downwardly extending from the base 21, and a semicircular guide portion 23 integrally connected with an end of the support 22.

The base 21 may be attachably or detachably coupled to the lower end of the handpiece 10 by means of a screw, for example. The support 22 performs a role of supporting the guide portion 23 such that the semicircular guide portion 23 is spaced apart from the base 21 by a predetermined distance under the base 21. The guide portion 23 may have a semicircular shape or a ring shape, and may be designed to allow the laser outputted from the handpiece 10 to pass through a central axis of the guide portion 23. Accordingly, the user may be guided to easily align the center of the guide portion 23 with a target onto which the laser is to be radiated.

Since the handpiece 10 and the tip 20 described above are well known in the related art, a detailed description thereof is omitted. In addition, it will be understood that embodiments of the present disclosure are not limited to the configurations of the handpiece 10 and the tip 20 illustrated in the drawings, and various changes can be made to the configurations. For example, although it is illustrated that the tip 20 is attached to the handpiece 10, a handpiece without the tip 20 may be used. In another example, the guide portion 23 of the tip 20 may have an annular shape, and the tip 20 may not include the support 22 and the guide portion 23.

In an embodiment, the handpiece 10 may further include a plurality of distance sensors 30. In the illustrated embodiment, the distance sensors 30 may be attached to a side surface of the base 21, being spaced apart from each other by a predetermined distance. In an alternative embodiment, the distance sensors 30 may be arranged on the circumference of the lower end of the handpiece 10. In another embodiment, the tip 20 may not be attached to the handpiece 10, and in this case, the plurality of distance sensors 30 may be attached to the circumference of the lower end of the handpiece 10 at predetermined intervals.

In an embodiment, the handpiece 10 may include two distance sensors 30. In this case, the distance sensors 30 may be arranged along the circumference of the lower end of the handpiece 10 (or the circumference of the base 21 of the tip 20) at intervals of 180 degrees. In an alternative embodiment, the handpiece 10 may include three distance sensors 30. In this case, the distance sensors 30 may be arranged along the circumference of the lower end of the handpiece 10 or the circumference of the base 21 at intervals of 120 degrees.

The number of distance sensors 30 is not specifically limited, and in a preferred embodiment, three or four distance sensors 30 may be installed. The distance sensors 30 may be infrared (IR) sensors or ultrasonic sensors or may be implemented by using sensors for measuring a distance in various other related-art methods.

On the assumption that the handpiece 10 to which the tip 20 is attached is disposed in the upright position with respect to a patient's skin S as shown in FIG. 3, a distance from the base 21 of the tip 20 to the skin S is represented by H, and a distance to the skin S measured by the distance sensors 30 attached to the side surface of the base 21 is represented by d. In this case, distances d measured by the plurality of distance sensors 30 are represented by d1, d2, d3, and so on.

Referring to FIG. 5, a laser device may include a handpiece 10, a distance sensor 30, a controller 40, and a laser generator 50. The handpiece 10 and the distance sensor 30 are the same as described above with reference to FIGS. 3 and 4, and thus a detailed description thereof is omitted.

The laser generator 50 is a device that generates a laser. The controller 40 may control output of the laser generated at the laser generator 50. The laser generator 50 may include a well-known laser generation device. For example, the laser generator 50 may be provided with elements including a well-known laser gain medium such as Nd:YAG, Alexandrite, luby, etc., a flash lamp, a reflector, a mirror, and a power supply unit. The flash lamp may be disposed in the proximity of the laser gain medium and may receive power from the power supply unit to radiate exciting light onto the gain medium. The reflector may be disposed to surround the flash lamp, and may allow the exciting light radiated from the flash lamp to be radiated onto the laser gain medium without a loss. When the laser gain medium receives the exciting light from the flash lamp, the light reciprocates between mirrors at both sides and causes amplification through stimulated emission, thereby generating laser light.

The laser generated at the laser generator 50 may be guided through the optical fiber 60, for example, and may be transmitted to the handpiece 10, and may be outputted through one end of the handpiece 10. In an alternative embodiment, the laser beam may be transmitted to the handpiece 10 in other ways rather than through the optical fiber 60. For example, instead of the optical fiber 60, a light guide arm provided with a plurality of mirrors may be disposed between the laser generator 50 and the handpiece 10, and the laser may be transmitted to the handpiece 10 through the light guide arm, or other well-known light guide means may be used. The controller 40 may control the output of the laser generated at the laser generator 50. In an embodiment, the controller 40 may receive a distance measurement signal value from the distance sensor 30 as a measurement signal, and, based on the distance measurement value, may transmit a control signal for controlling the laser output to the laser generator 50 and may control the laser output.

In an embodiment, the controller 40 may calculate an effective area, which is a region of a target onto which the laser is really radiated, based on distances d to the target measured by the plurality of distance sensors 30, and may control to increase and reduce the laser output to radiate the laser onto the effective area with a predetermined energy density.

According to an exemplary method for calculating the effective area, the controller 40 may calculate a slope of the handpiece to the target and a distance between the target and the handpiece, based on the measured distance d to the target, and may calculate the effective area of the target based on the slope of the handpiece and the distance. For example, the controller 40 may pre-store information regarding characteristics of the output laser, such as an output angle and a diameter of the laser outputted from the handpiece 10, and may calculate the effective area of the target based on the information regarding the characteristics of the laser and the calculated values regarding the slope of the handpiece and the distance.

When the effective area of the target is calculated, an energy density of the currently outputted laser can be known. Therefore, it can be known how much the laser output should be increased or reduced in order to output the laser with a predetermined target energy density, and the controller 40 may control the laser output according to a value calculated in this way, such that the laser can be radiated onto the effective area of the target with the predetermined energy density.

Figure 6:
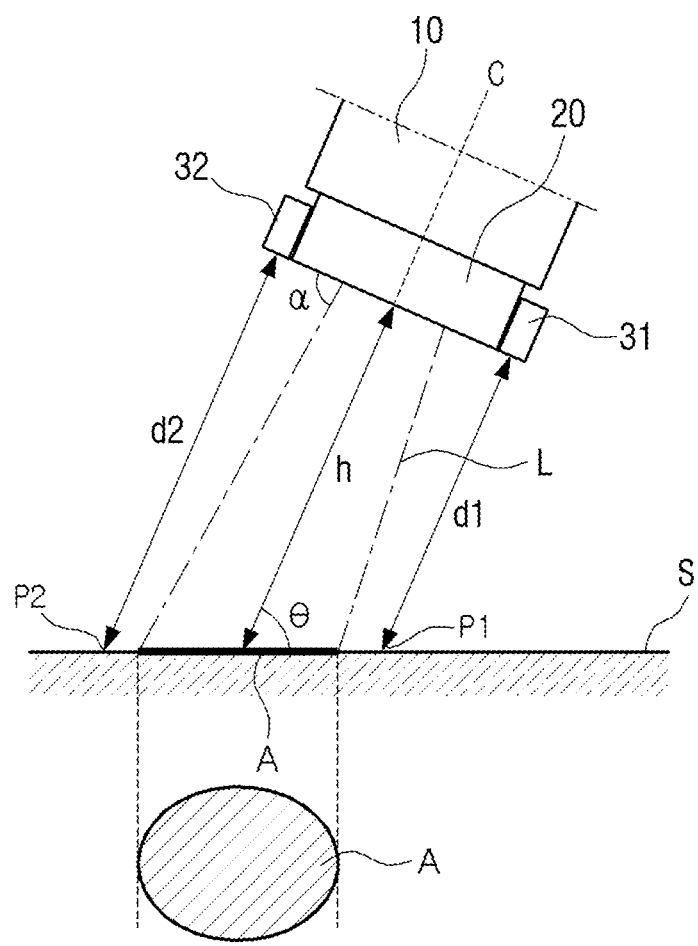
FIG. 6 is a view showing an example of a laser form when the handpiece is titled and radiates a laser.

Hereinafter, an exemplary laser output control method of the controller 40 will be described with reference to FIGS. 6 and 7. It is assumed that the handpiece 10 is tilted with respect to a patient's target (skin S) by a predetermined angle θ as shown in FIG. 6, and radiates a laser L. For convenience of explanation, the support 22 and the guide portion 23 of the tip 20 are omitted and only two distance sensors 31, 32 are illustrated. It is assumed that the handpiece 10 is designed to output a collimated beam, but the really outputted laser L does not have a complete collimated beam form, and has a predetermined output angle α and the handpiece 10 is distanced from the target by a predetermined distance h. In this case, it is assumed that the distance h between the target and the handpiece 10 refers to a distance from the lowermost portion of the handpiece 10 to the target along the central axis C of the handpiece 10 (In this case, it is assumed that the central axis C is the same as that of the laser L).

Figure 7:
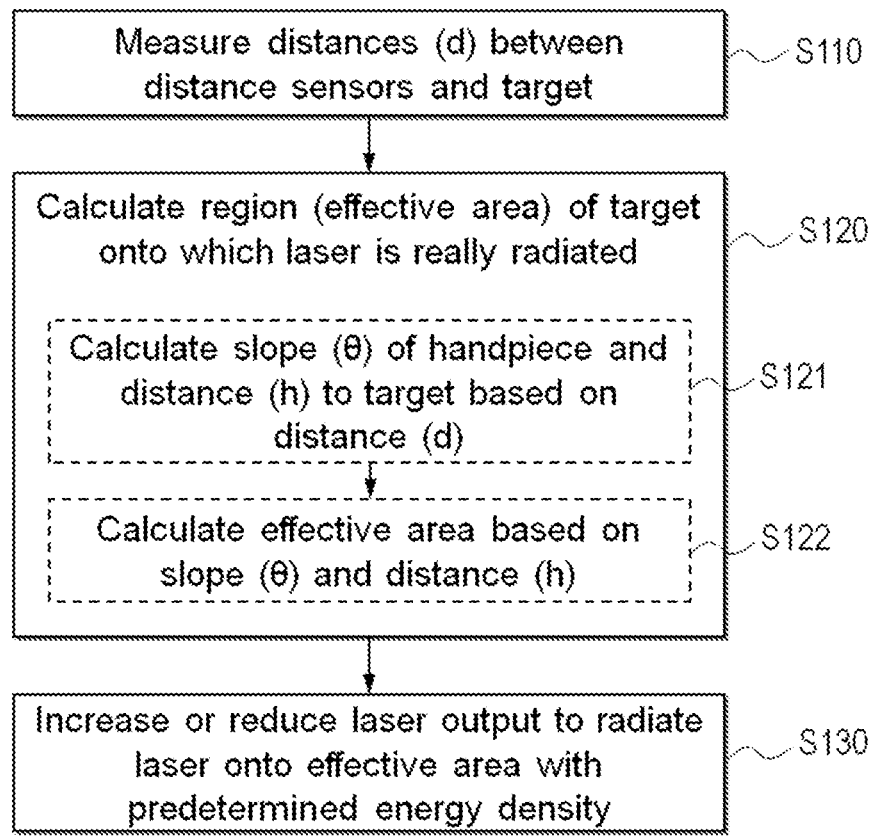
FIG. 7 is a view to explain a laser output control method according to an embodiment of the present disclosure.

Referring to an exemplary flowchart of the laser output control method shown in FIG. 7 on this assumption, distances between the distance sensors 31, 32 and the target are measured, first, at step S110. Herein, the "distance between the distance sensor and the target" refers to a distance from each distance sensor 31, 32 to the target (that is, the skin S) along a line parallel to the central axis C (or the central axis of the laser L) of the handpiece 10. For example, referring to FIG. 6, the first distance sensor 31 may measure a distance d1 to a first point P1 of the skin S, and the second distance sensor 32 may measure a distance d2 to a second point P2 of the skin S. Although not shown, additional distance sensors such as third and fourth distance sensors may be installed, and accordingly, the distance sensors may measure distances d3, d4, . . . to the skin.

Thereafter, at step S120, an effective area which is a region of the target onto which the laser is radiated may be calculated based on the distances d1, d2, d3, . . . between the distance sensors 31, 32 and the target. Herein, the "effective area" refers to a region of the target (skin) onto which the laser L is really radiated, that is, a region indicated by "A" in FIG. 6.

There may be various methods for calculating the effective area A based on the distances d1, d2, . . . measured by the distance sensors 31, 32. In the exemplary method of calculating the effective area A in the embodiment of FIG. 7, the slope θ of the handpiece 10 and the distance h to the target are calculated based on the distances d1, d2, . . . at step S121. Herein, the slope θ refers to a slope of the central axis C of the handpiece 10 (or the central axis of the laser L) with respect to the target (that is, the skin S), and the distance h to the target may refer to a distance between the lowermost portion of the handpiece 10 and the target along the central axis C.

In an embodiment, since a mutual arrangement relationship among the plurality of distance sensors 31, 32, . . . is already known, characteristics of an oval (for example, a length of a major axis, a length of a minor axis, an area, etc.) passing through the plurality of points P1, P2, . . . may be calculated based on the distances d1, d2, . . . measured by the distance sensors 31, 32, . . . , and accordingly, it may be calculated how much the handpiece 10 is tilted with respect to the target, and how long the handpiece 10 is distanced from the target, based on the characteristics of the oval and the measurement values d1, d2, . . . of the distance sensors.

In this case, in an embodiment, data related to the relative arrangement relationship among the plurality of distance sensors 31, 32, . . . may be pre-stored in a storage means (for example, a memory), and the characteristics of the oval passing through the points P1, P2, . . . according to distances d1, d2, . . . measured by the distance sensors based on the arrangement relationship may be pre-stored in the form of a lookup table, for example. In addition, the slope θ of the handpiece and the distance h calculated based on the characteristics of the oval may be pre-stored in the form of a lookup table, for example.

When the slope θ of the handpiece and the distance h are calculated, an area onto which the laser L is radiated, that is, the effective area A, may be calculated based on the slope θ and the distance h at step S122. That is, when it is assumed that the characteristics of the laser L (for example, information including an output angle α, a cross-sectional area, etc.) outputted from the handpiece 10 are already known, the effective area A may be calculated based on the laser characteristics and the slope θ of the handpiece and the distance h. In this case, for example, the effective area A calculated based on the characteristics of the laser (the output angle α, the cross-sectional area, etc.), and the slope θ of the handpiece and the distance h may be stored in the form of a lookup table, or the effective area A may be calculated and derived from a predetermined equation having the laser characteristics and the slope θ of the handpiece and the distance h as variables.

When the effective area A of the target is calculated in the above-described method, the laser output may be increased or reduced to radiate the laser L onto the effective area A with a predetermined energy density. That is, the predetermined energy density of the laser may refer to, for example, an energy density on an effective area (hereinafter, referred to as a "reference effective area") that is obtained when the handpiece 10 is distanced from the target (skin S) by a predetermined distance H in the upright position as shown in FIG. 1, and accordingly, the laser output may be controlled to maintain the same energy density by comparing the effective area A obtained when the handpiece 10 is tilted with respect to the target by the predetermined slope θ and is distanced by the predetermined distance h, and the reference effective area.

The laser output control method for constantly maintaining the energy density received by the target has been described as an exemplary method of FIG. 7. However, the laser output may be controlled in other methods. For example, in the illustrated embodiment, the method for calculating the effective area by calculating the slope θ of the handpiece and the distance h based on the distances d1, d2, . . . measured by the distance sensors has been described. However, in another alternative embodiment, the effective area may be calculated without calculating the slope θ of the handpiece or the distance h. Therefore, it will be understood by a person skilled in the art that the method of FIG. 7 is merely an exemplary method for obtaining an effective area.

In addition, in an embodiment, the operation of calculating the effective area based on the distances d1, d2, . . . measured by the distance sensors may be performed in the controller 40, but, in an alternative embodiment, an entirety or a portion of the calculating operation may be performed in a separate calculation unit (not illustrated). That is, when the controller 40 or the distance sensors 30 transmit the distance measurement values d1, d2, . . . to the calculation unit, the calculation unit may calculate the effective area A and may transmit the effective area to the controller 40.

In a preferred embodiment, the controller 40 may control to temporarily turn on/off the laser output based on one or more distance values d1, d2, . . . measured by the distance sensors. For example, there may be a risk of an accident when the handpiece 10 outputs a laser in a state in which the handpiece 10 is not oriented toward the target S and is oriented toward another person or object, and also, when the user excessively tilts the handpiece 10 and the handpiece 10 radiates the laser onto the target in this state, there may be a problem that a predetermined medical/beauty care effect is not obtained. Accordingly, in an embodiment of the present disclosure, to solve the above-mentioned problems, the controller 40 may control to turn on/off the laser output based on the distances d1, d2, . . . measured by the distance sensors.

For example, when at least one value of the distances d1, d2, . . . measured by the plurality of distance sensors 31, 32 is longer than or equal to a predetermined distance, the controller 40 may determine that the handpiece 10 is very far from the target or the handpiece 10 is oriented toward an object rather than the target, and may turn off the laser output.

In another example, when the slope θ of the handpiece 10 is less than or equal to a predetermined angle, the controller 40 may determine that the handpiece 10 is excessively tilted and is oriented toward the target, and thus determine that a desired medical/beauty care effect may not be obtained, and may turn off the laser output.

In this case, the controller 40 may inform the user of the temporary turning off of the laser output by using a warning sound or flashing on or off a warning lamp, and, when the distances d1, d2, . . . or the slope θ falls within a normal range, the controller 40 may inform the user of this by using a sound or flashing on or off a lamp.

It will be understood by a person skilled in the art that various modifications or change can be made based on the descriptions of the present disclosure. Therefore, the scope of the present disclosure is defined not by the detailed description of the present disclosure but by the appended claims and equivalents thereto.

What is claimed is:

1. A method for controlling a laser output of a laser device provided with a laser generator and a handpiece for radiating a laser generated at the laser generator onto a target, the method comprising the steps of:
   measuring, by a plurality of distance sensors arranged along a circumference of one end of the handpiece from which the laser is outputted, distances d between the plurality of distance sensors and the target;
   calculating an effective area which is a region of the target onto which the laser is really radiated, based on the distances d between the distance sensors and the target; and
   increasing or reducing the laser output to radiate the laser onto the effective area with a predetermined energy density,
   wherein the plurality of distance sensors comprise three or more sensors, and the plurality of distance sensors are arranged along the circumference of the one end of the handpiece at predetermined intervals.

2. The method of claim 1, further comprising a step of stopping the laser output when a distance measured between any one of the plurality of distance sensors and the target is longer than or equal to a predetermined distance.

3. The method of claim 1, wherein the step of calculating the effective area of the target comprises the steps of:
   calculating a slope $\theta$ of the handpiece with respect to the target and a distance h between the target and the handpiece, based on the measured plurality of distances d; and
   calculating the effective area of the target based on the slope $\theta$ of the handpiece and the distance h.

4. The method of claim 3, wherein the step of calculating the effective area of the target comprises calculating the effective area of the target according to the slope $\theta$ of the handpiece and the distance h, based on an output angle $\alpha$ and a diameter of the laser outputted from the handpiece.

5. The method of claim 3, further comprising a step of stopping the laser output when the calculated slope $\theta$ of the handpiece is less than or equal to a predetermined angle.

6. The method of claim 1, wherein the laser outputted from the handpiece is a collimated beam, a focused beam, or a defocused beam.

7. A laser device comprising:
   a laser generator configured to generate a laser;
   a controller configured to control an output of the laser generated at the laser generator;
   a handpiece configured to output the laser generated at the laser generator through one end thereof; and
   a plurality of distance sensors attached along a circumference of the one end of the handpiece,
   wherein the controller is configured to calculate an effective area which is a region of a target onto which the laser is really radiated, based on distances d to the target measured by the plurality of distance sensors, and to increase or reduce a laser output to radiate the laser onto the effective area with a predetermined energy density, and
   wherein the plurality of distance sensors comprise three or more sensors, and the plurality of distance sensors are arranged along the circumference of the one end of the handpiece at predetermined intervals.

8. The laser device of claim 7, wherein the controller is configured to stop the laser output when a distance measured between any one of the plurality of distance sensors and the target is longer than or equal to a predetermined distance.

9. The laser device of claim 7, wherein the controller is configured to calculate a slope $\theta$ of the handpiece with respect to the target and a distance h between the target and the handpiece, based on the measured distances d to the target, and to calculate the effective area of the target based on the slope $\theta$ of the handpiece and the distance h.

10. The laser device of claim 9, wherein the controller is configured to calculate the effective area of the target according to the slope $\theta$ of the handpiece and the distance h, based on an output angle $\alpha$ and a diameter of the laser outputted from the handpiece.

11. The laser device of claim 9, wherein the controller is configured to step the laser output when the calculated slope $\theta$ of the handpiece is less than or equal to a predetermined angle.

12. The laser device of claim 7, wherein the laser outputted from the handpiece is a collimated beam, a focused beam, or a defocused beam.

* * * * *